US005785943A

United States Patent [19]
Guillet et al.

[11] Patent Number: 5,785,943
[45] Date of Patent: Jul. 28, 1998

[54] PRODUCTION OF HYDROGEN PEROXIDE

[76] Inventors: James E. Guillet, 31 Sagebrush Lane, Don Mills, Ontario, Canada, M3A 1X4; Gad Friedman, 3 Hazait Street, Rehovot 76349, Israel

[21] Appl. No.: 323,423

[22] Filed: Oct. 14, 1994

Related U.S. Application Data

[63] Continuation-in-part of Ser. No. 136,020, Oct. 14, 1993, Pat. No. 5,374,339.

[51] Int. Cl.[6] .............. B05D 7/24; B32B 17/02; B32B 18/00; C01B 15/023

[52] U.S. Cl. .............. 423/588; 427/220; 428/403; 428/405; 428/406

[58] Field of Search .............. 502/150, 167, 502/168; 252/182.12, 182.3; 423/588; 427/220; 428/405, 406, 403, 404

[56] References Cited

U.S. PATENT DOCUMENTS

| | | | |
|---|---|---|---|
| 4,349,526 | 9/1982 | Goor et al. | 423/588 |
| 4,393,038 | 7/1983 | Sun et al. | 423/584 |
| 4,415,631 | 11/1983 | Schutijser | 502/150 |
| 4,576,687 | 3/1986 | Hertl et al. | 204/157.5 |
| 4,946,566 | 8/1990 | Stevens et al. | 204/157.5 |
| 5,374,339 | 12/1994 | Guillet et al. | 423/588 |

OTHER PUBLICATIONS

Mahmoud, Mohamed E., Gohar, Gamal A., "Synthesis of Silica–Bound Complexing Agents Containing Diaminoanthraquinones and Their Metal–Uptake Properties", *Alexandria Eng. J.*, 33(4), D159–D165 (English), Oct. 1994.

Tickle and F. Wilkinson, Trans. Farad, Soc., 61, pp. 1981–1990 (Apr., 1965).

*Primary Examiner*—Wayne Langel
*Attorney, Agent, or Firm*—Ridout & Maybee

[57] ABSTRACT

Hydrogen peroxide is produced by a process which uses solid, insoluble, supported anthraquinone as catalyst. The supported anthraquinone is converted to supported anthrahydroquinone utilizing soluble reducing agentsor by hydrogenation with a hydrogen-donating organic substrate such as an alcohol, followed by reaction with oxygen, to regenerate anthraquinone and to form hydrogen peroxide, which can be solvent extracted from the solid catalyst.

17 Claims, No Drawings

PRODUCTION OF HYDROGEN PEROXIDE

CROSS REFERENCE TO RELATED APPLICATIONS

This is a continuation-in-part of U.S. patent application Ser. No. 08/136,020, filed Oct. 14, 1993, now U.S. Pat. No. 5,374,339.

FIELD OF THE INVENTION

This invention relates to anthraquinone catalyzed chemical processes and novel forms of anthraquinone for use therein. More particularly, it relates to methods for manufacture of hydrogen peroxide, using novel forms of anthraquinone as catalyst.

The photochemical reaction between alcohols and oxygen sensitized by quinone catalysts has been studied for a number of years. For example, Tickle and Wilkinson[1] studied the photooxidation of isopropanol (2-propanol) using anthraquinone (AQ) as a catalyst. The overall stoichiometry of the reaction is

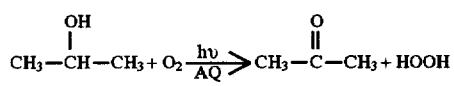

The mechanism is proposed to involve the photoreduction of AQ via its triplet state to form anthrahydroquinone which is converted back to the starting catalyst AQ with air or oxygen with the concurrent formation of HOOH.

An analogous reaction involving the catalytic reduction of an alkyl anthraquinone by hydrogen is the basis of a current industrial synthesis of hydrogen peroxide (HOOH) via the reaction sequence

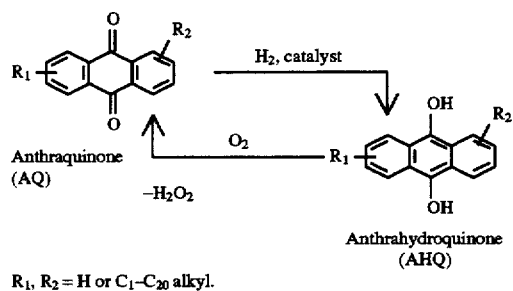

$R_1$, $R_2$ = H or $C_1-C_{20}$ alkyl.

Hydrogen peroxide is an important industrial chemical. It is widely used as a bleach, e.g. in the pulp and paper industry. It is also used extensively in the mining industry, e.g. for removing cyanide residues from gold mining operations. It is basically an environmentally acceptable chemical, unlike many competitive industrial bleaching compounds. Hydrogen peroxide is however a difficult material to transport safely. The locations where it is to be used industrially, e.g. mining sites and pulp mills, are often far removed from other chemical manufacturing and processing facilities. The production of the required hydrogen peroxide on site is accordingly desirable.

AQ derivatives are widely used in industrial processes for the production of hydrogen peroxide. A process using AQ solution as working solution is normally employed. The AQ derivative is hydrogenated in solution to anthrahydroquinone (AHQ), using a solid metal hydrogenation catalyst. The AHQ is subsequently oxygenated to AQ, with generation of hydrogen peroxide. There are numerous problems with this known process, which detract from its economic performance. For example, separation of the dissolved AQ from the product solution of hydrogen peroxide is complicated and costly. Liquid-liquid extraction, to take out the hydrogen peroxide product as an aqueous solution, is necessary. This is costly, and involves large volumes of recycle. Quantitative separation is not achieved. Significant losses of AQ during the recovery process are inevitable. Only dilute solutions of hydrogen peroxide are obtained, unless subsequent distillation is undertaken.

Moreover, extreme precautions need to be taken in operating the process, particularly when air or oxygen is used as the oxidizing agent to generate the hydrogen peroxide. Blowing air or oxygen into solutions of organic chemicals is a dangerous operation. The dangers are increased when, as is common in hydrogen peroxide production processes using AQ as catalyst, colloidal or solid metal is used as the hydrogenation or reduction catalyst. If this catalyst becomes mixed with the reaction mixture of the oxidation stage, potentially explosive conditions may be created. The entire prior art process needs to be conducted under very carefully controlled conditions. This further adds to the expense of conducting the process, and contributes to the large investments and high operating costs of the plant. Complicated distillation is required in order to purify the hydrogen peroxide and to concentrate it to reduce shipment volumes.

It is an object of the present invention to provide novel methods of conducting anthraquinone-catalyzed chemical processes, which overcome or at least reduce one or more of the aforementioned disadvantages.

It is a further object to provide a novel process for production of hydrogen peroxide.

It is a further object to provide novel forms of anthraquinone useful in conducting such processes, and methods for preparing such novel forms of anthraquinone.

SUMMARY OF THE INVENTION

This invention provides an anthraquinone (AQ) moiety immobilized on an inert, macromolecular carrier, and methods for its preparation. The immobilized AQ maintains substantially all of its chemical reactivity. Thus it can be utilized for most of the chemical procedures in which AQ has previously been proposed for use as a catalyst. Moreover, as a solid moiety insoluble in the liquid reaction media in which such processes are commonly conducted, at least under the chosen product recovery conditions, it can be easily separated from the products and other residual reactants, and recycled for re-use. Recoveries are substantially quantitative, thereby significantly improving the economics of the processes in which it is used.

In addition, no harmful vapours of AQ are generated during use of the immobilized AQ of the invention. Further, the use of colloidal metal catalysts in the reduction stage is avoided in processes of the invention which utilize the novel supported AQ compositions, thereby further simplifying and improving the economics of the process.

The term "macromolecular" as used herein with reference to the supports used in the present invention is intended to embrace inorganic high molecular weight materials such as various forms of silica (glass beads and rods, silica gels, particulate silica etc.) as well as organic polymers such as polyethylene, cellulose, etc.

Examples of processes where this novel, immobilized AQ can be used include: photochemical oxidation of alcohols, photochemical production of hydrogen peroxide, formation of hydrogen peroxide by chemical reduction, hydrogenation of the AQ with homogeneous catalysts followed by air oxidation, and other radical reactions initiated by hydrogen abstraction, photochemical or otherwise.

The immobilized AQ is able to undergo a multitude of reaction cycles retaining its activity and efficiency for a large number of turnovers; thus it can be regarded as a true catalyst.

The process of the present invention very significantly reduces the problems of separation and recovery of the AQ catalyst from the product, while maintaining the activity of the AQ moiety. Generally the immobilized AQ catalyst of the present invention is insoluble in the reaction solvent under all conditions of operation. Essentially, however, it needs to be insoluble under the conditions at which the product solution is recovered, so as to provide the benefits of ease of separation.

The process of the present invention offers several advantages over the current methods involving the AQ-AHQ cycle.

(a) The immobilization of AQ onto the macromolecular supports prevents significant consumption or loss of this material during the process. It is easily retrieved when the reaction is stopped, and avoids contamination of the working solutions and effluents.

(b) AQ immobilized on the totally inert inorganic supports, which are preferred in the present invention, has a special advantage over similar products where organic polymers are utilized as carriers. This is manifested, for example, in the photochemical process. AQ which was chemically attached to an organic polymer exhibited spectroscopic evidence for the reversible photochemical reduction and air oxidation as observed in organic AQ solution. However, the reactive intermediates attack the supporting polymer, consuming its available hydrogen atoms.[2] This is not the case with inert inorganic supports.

(c) Tedious separation of reactants and products is greatly simplified.

(c) The ability of the immobilized AQ to function in aqueous and in polar and non polar organic solutions is of particular interest and significance. The common industrial process for hydrogen peroxide manufacture is complicated by changes in the reagent's solubility. AQ is soluble in organic non-polar solvents. The AQ is hydrogenated to form AHQ which is soluble in organic polar solvents. Oxygen is blown in, and the AHQ is transformed back to AQ, changing the solubility characteristics thereof, while releasing hydrogen peroxide. The hydrogen peroxide is collected by extraction with water. Special efforts need to be made to overcome the solubility problems and to minimize AQ losses. The immobilized AQ used in the process of the present invention, especially the preferred inorganic-supported AQ can be integrated into the current process of HOOH manufacture. It bypasses these complications. It is active in aqueous as well as organic solutions. No losses of immobilized AQ to the solvents have been observed.

This invention has the potential for producing hydrogen peroxide photochemically, using natural hydroxy compounds (alcohols, carbohydrates, polycarbohydrates) as hydrogen donors, thus enabling the preparation of this important chemical where light and the above-mentioned raw materials are abundant. Alternatively, these alcohols can be utilized to reduce the carbonyl functions of AQ in a catalyzed transfer hydrogenation reaction.[3]

DESCRIPTION OF THE PREFERRED EMBODIMENTS

One preferred aspect of the present invention is thus solid AQ compounds in which an AQ moiety, optionally derivatized or substituted, is covalently bonded to a solid inorganic support, suitably silica gel or glass, e.g. in the form of beads. The inert support is amine functionalized. Anthraquinone compounds carrying appropriately selected functional groups for reaction with the amine groups on the inorganic support are reacted therewith, to form the solid supported catalysts of the present invention. Specific examples of such anthraquinone compounds are anthraquinone carboxylic acid, anthraquinone carboxylic acid chloride [AQCOCl], anthraquinone 2-sulphonyl chloride [AQ-2-$SO_2$Cl] and anthraquinone 2,6-disulphonyl chloride [AQ-2,6-$SOCl_2$].

The invention includes methods to activate silica or glass in the form of beads, loose powder, fibres, tubes or plates by using silane coupling molecules, e.g., amino propyl trimethoxy silane (APTS), and a method to bind AQ thereto, using AQ derivatives discussed above. Anthraquinone (for example as AQ carboxylic acid chloride) may be covalently bound to the free amino functions which have thus been attached to the silica/glass. The amount of AQ immobilized by this method relates to the accessible surface area of the silica/glass. High densities of amino groups can be obtained by proper choice of technique.

Whilst inorganic macromolecular supports are preferred, organic polymeric supports which are sufficiently inert towards the reactants and products can also be used. Examples of suitable such polymers include cellulose, e.g. in the form of paper, and polyethylene. Cellulose has suitable available hydroxy groups for derivatization to attach the AQ moieties thereto. Polyethylene can be rendered suitable for derivatization by known techniques of activation such as irradiation.

Alternatively, an AQ (e.g., in the form of 2-isopropenyl carboxylic acid or AQCH=CHCOOH) moiety can be copolymerized with, e.g., acrylic acid or any of its derivatives. This polymer is attached to the amine activated silica via its functional group—the carboxylic group—with the aid of coupling agents such as dicyclohexyl carbodiimide (DCC). This approach enables heavier loading of AQ on silica. Moreover, changing the co-monomer can provide AQ catalysts with varying affinity and effectivity towards solvents and substrates.

In a similar process, the silica may be functionalized with β-(trimethoxysilicyl)propyl methacrylate followed by polymerization with a mixture of vinyl AQ and co-monomer.

In addition to anthraquinone-2-carboxylic acid derivatives, other suitable quinoid systems can be utilized to perform similar reactions. Among those are anthraquinone-2-sulfonic acid (AQ-2-$SO_3$H), 2,6- or 1,5-disulfonic acid (AQ-2,6-di$SO_3$H; AQ-1,5-di$SO_3$H) and their derivatives and other members of the anthraquinone group substituted by electron-withdrawing moieties such as chlorine atoms, and also benzoquinone and benzanthrone.

In one preferred method of application of this invention, photochemical procedures are adopted. The immobilized AQ is suspended in the liquid substrate, which is the hydrogen donor. Air is blown through this suspension in order to stir it and to supply oxygen. Irradiation at 360 nm or shorter wave length induces photoreduction of the immobilized AQ to AHQ. In the presence of air or oxygen, this is subsequently oxygenated to yield hydrogen peroxide and the hydrogen-donating co-reagent is concurrently oxidized. For example, irradiation of immobilized AQ in isopropanol leads to the formation of hydrogen peroxide and acetone. The reaction can take place in a suspension of the pure co-reagent or in its aqueous solution.

Several organic alcohols have displayed this hydrogen donor ability: primary alcohols (ethanol and n-butanol), secondary alcohols (isopropanol and sec-butanol), polyols (glycerol and the sugars sucrose and xylose).

The process of the invention can also be performed in two distinct and separate stages. For example, the hydrogen abstraction or reduction can be performed (in the absence of oxygen) in a solution of hydrogen donor, e.g. isopropanol, which can be then removed from the solid phase, supported AQ catalyst. Hydrogen peroxide can be harvested from the solid catalyst in a second medium, e.g. water, after exposure to oxygen. This route of alternating reaction media has the advantage of collecting the hydrogen peroxide in a preselected medium, free from starting materials.

One can also obtain high yields of hydrogen peroxide photochemically by continuous irradiation in the presence of air. This process is believed to take place via the excited triplet state of the anthraquinone moiety and these excited states are known to be quenched by oxygen. It appears that the rate of photoreduction on these highly active catalysts can compete effectively with quenching by oxygen.

When the process is conducted non-photochemically, the immobilized AQ is preferably converted to AHQ with the aid of soluble reducing agents selected from the large group of such agents which are known in the art to be effective carbonyl group reducing agents. Examples include sodium borohydride, sodium dithionite, sodium cyanoborohydride, and sodium sulfite, using either aqueous or non-aqueous media. This reduction proceeds smoothly, under mild conditions. The reduced species (immobilized AHQ) may be washed free of excess reagents. Air may be blown through it so as to regenerate AQ and produce hydrogen peroxide, which can be drained off as a solution.

In an alternative, the immobilized AQ may be reduced to immobilized AHQ by hydrogenation using homogeneous catalysts. A large number of suitable such catalysts are known. Many of them are characterized by their ability to catalyze the reduction of carbonyl compounds under a variety of working conditions of temperature, pressure, solvents, etc. Others have been studied and reported in connection with anthraquinone hydrogenation. Examples include ruthenium triphenylphosphine complexes, cobalt pentacyanide (in water), palladium chloride (in DMF), and a variety of others reported in the scientific literature (see references 4 below). Immobilized AHQ so formed can be washed in an inert atmosphere, and suspended in water. Blowing of air brings about AQ and hydrogen peroxide formation.

The basic reactions and structures can be represented as follows:

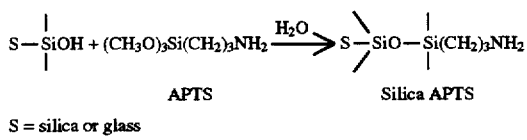

APTS  Silica APTS

S = silica or glass

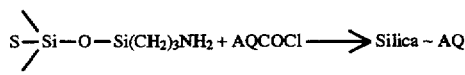

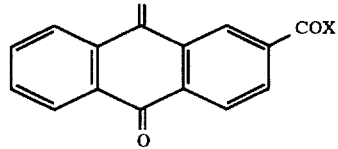

X = OH – Anthraquinone-2-carboxylic acid AQCOOH
Y = Cl – Anthraquinone-2-carboxylic acid chloride AQCOCl

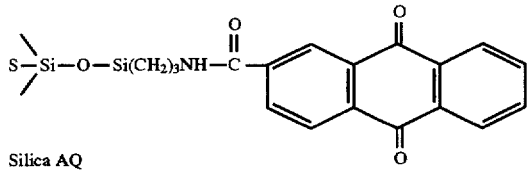

Silica AQ

The following working examples represent a large number of catalytic reactions which can be utilized for the production of hydrogen peroxide with immobilized AQ. They were conducted in small volumes, and demonstrate the feasibility of these processes. They are not optimized for use on a large, commercial scale, and rigorous exclusion of oxygen from the washings, absolute removal of catalyst, reducing agent etc. was not undertaken. Accordingly the reported yields should be regarded as the minimums attainable, before process optimization.

EXAMPLE 1

Activation of Silica-Gel Beads

Aminopropyl trimethoxysilane (APTS, 2 g) was added to 100 ml of water. Acetic acid was added dropwise to pH 4. After brief stirring, 20 g of silica gel beads (60–120 mesh, BDH) were added. After one hour the aqueous solution was decanted. The silica was washed with water and ethanol, and air dried overnight. These activated beads were further reacted with AQ derivatives (see examples below) and have over 0.11 mmol free amine/g as evidenced by the amount of binding.

Higher densities of amino groups can be obtained by refluxing silica with APTS in toluene.

EXAMPLE 2

Activation of Glass Fibres

Pyrex glass fibres (5 g) were treated with sodium hydroxide (20% solution) for ca. 30 min. at room temperature. The base was rinsed and the fibres washed thoroughly with water, dilute hydrochloric acid, and ethanol, and then air dried. The fibres were than treated with an aqueous APTS mixture as described in Example 1.

EXAMPLE 3

Binding of AQCOCl to Fumed Silica

Fumed silica (Cab-o-Sil MS, Cabot Corp., 5 g, activated with APTS, as described in Example 1 and dry tetrahydrofuran (THF, 50 mL) was stirred in a flask. AQCOCl (220 mg) in 10 mL of THF was added dropwise. After 30 min., ca. 0.5 mL of pyridine was added and the mixture stirred for an additional 1 hour. The modified silica was filtered, thoroughly washed with ethanol, and then dried. The washings contained about 50 mg of AQCOOEt and AQCOOH (as determined by UV absorption at 324 nm) indicating that ca. 0.126 mmol/g of AQ was immobilized on the surface of the silica.

EXAMPLE 4

Binding of AQCOCl to Silica Gel

Silica gel 60 (5 g, 230–400 mesh, EM Science, APTS activated as in 1) was reacted with 165 mg AQCOCl as in Example 3. Analysis of the washing shows that 159 mg (0.11 mmol/g) AQ were bound to the silica beads.

EXAMPLE 5

Binding of AQCOCl to Pyrex Glass Fibres

Pyrex glass fibres activated with APTS (5 g) were reacted with AQCOCl (55 mg) by procedure of Example 3. Analysis of the washings determined that 35 mg (0.026 mmol/g) of AQ was bound.

EXAMPLE 6

BiO glass 1500 (porous glass for chromatography, Bio-Rad) was reacted with AQCOCl by the procedure of Example 3. Bound AQ⁻ 0.045 mmol/g.

EXAMPLE 7

Binding of AQCOCl to Cellulose

Cellulose pulp (2 g) was stirred in water for 24 hours. The water was removed and the pulp soaked in dry methanol. Methanol was drained off and a new portion was added. This was repeated four times, followed by similar cycles using dry THF. Finally, 10 mg of AQCOCl was added. After 5 hours a few drops of pyridine was added and the mixture was stirred overnight. Analysis of the washings indicates that 0.01 mmol of AQ was bound to the pulp.

EXAMPLE 8

Binding of AQCOOH to Silica Gel

Dry aminopropyl-functionalized silica gel (3 g, Aldrich, ~9% functionalized) was suspended in 75 mL dry THF. AQ-COCL (404 mg, 1.5 mmol) was added and the mixture was stirred under dry conditions. Pyridine (0.5 mL) was added after 1 h, and the mixture was stirred for an additional 12 h. The loaded silica was filtered, washed with acetone, ethanol, water and ethanol, and then dried. Analysis of the washings showed that 1.18 g (0.94 mmol/g) AQ were bound to the silica. This supported catalyst is designated I in Examples 20, 21 and 22 below.

EXAMPLE 9

Binding of AQ-2-SO₃H to Silica

AQ-2-SO₃Na (Aldrich) was converted to AQ-2-CO₂Cl with the aid of thionyl chloride.[5] The chloride (0.3 g, 1 mmol) was reacted with 4 g of aminopropyl-functionalized silica in THF. After 1 h, pyridine (0.5 mL) was added. The mixture was stirred for 12 h, filtered, washed with EtOH, and then dried. Examination of the washings showed that the binding was nearly complete, i.e., 0.25 mmol/g). This supported catalyst is designated II in Examples 20, 21 and 22 below.

EXAMPLE 10

Binding of AO-2,6-diSO₃H to Silica

AQ-2,6-diSO₃Na was converted to AQ-2,6-diSO₂Cl.[5] To a stirred suspension of aminopropyl-functionalized silica (3 g) in THF, was added 0.33 g (0.15 mmol) of the dichloride. After 1 h, pyridine (0.5 mL) was added and the mixture was stirred for an additional 12 h. Silica particles were filtered, washed with acetone, then with dilute Na₂CO₃, acetone and dried. Analysis of the washings showed that the whole amount was practically bound, i.e. loading of 0.25 mmol/g. This supported catalyst is designated III in Examples 20, 21 and 22 below.

EXAMPLE 11

Irradiation of Silica-AQ with Alcohols and Water Alcohol Mixtures

The irradiation experiments were performed in a Pyrex tub-shaped reactor equipped with a fritted glass at the bottom, an inlet side-arm and a tap. Air or nitrogen was supplied through the side-arm and the fritt, stirring the reaction mixture and forming either an oxidative or inert atmosphere.

Alternatively, these gases were supplied via the top forcing the liquid out while maintaining the desired atmosphere. A condenser at the top prevented loss of volatiles. This reactor was placed in a Rayonette irradiation well apparatus equipped with 16 360-nm lamps. Air was bubbled via the fritted glass and coolant was circulated in the condenser.

Irradiation experiments were carried out for 1–2 h. The amount of H₂O₂ produced was determined by an iodometric method for the organic reaction mixtures. The aqueous solutions were analyzed via titanate formation.[6] Several experimental examples are summarized in Table 1.

TABLE 1

HYDROGEN PEROXIDE FORMATION BY IRRADIATION OF IMMOBILIZED AQ WITH ALCOHOLIC HYDROGEN DONORS

| | Catalyst (mg) | Substrate | Irradiation (h) | H₂O₂ mol (mmol) | H₂O₂/ mol AQ |
|---|---|---|---|---|---|
| (a) | 120[a] | iPrOH | 1 | 0.32 | 33 |
| (b) | 100[a] | iPrOH (40% in H₂O) | 1 | 0.14 | 17 |
| (c) | 100[a] | iPrOH (20% in H₂O) | 1 | 0.1 | 12 |
| (d) | 120[a] | iPrOH | 2 | 0.47 | 60 |
| (e) | 100[a] | nBuOH | 1 | 0.3 | 37 |
| (f) | 100[a] | 2-BuOH | 1 | 0.19 | 24 |
| (g) | 100[a] | Ethanol | 1 | 0.38 | 47 |
| (h) | 100[a] | nBuOH (20% in H₂O) | 1 | 0.05 | 6 |
| (i) | 100[a] | 2-BuOH (20% in H₂O) | 1 | 0.01 | 1 |
| (j) | 100[a] | Ethanol (20% in H₂O) | 1 | 0.02 | 2.5 |
| (k) | 100[a] | Glycerin (20% in H₂O) | 1 | 0.03 | 3.6 |
| (l) | 100[a] | Sucrose (20% in H₂O) | 1 | 0.02 | 2.4 |
| (m) | 655[a] | iPrOH | 1 | 0.02 | 40 |
| (n) | 655[b] | H₂O | 1 | >0.004 | |
| (o) | 100[d] | xylose (5% in H₂O) | 1 | 0.0053 | 2 |
| (p) | 100[c] | sucrose (5% in H₂O) | 1 | 0.253 | 11 |
| (q) | 100[c] | iPrOH (40% in H₂O) | 1 | 2.464 | 110 |
| (r) | 500[c] | xylose (5% in H₂O) | 1 | 0.3 | 2.4 |

[a]Cab-o-sil M5: AQ content, 0.08 mmol/g, as made in Example 3.
[b]Cellulose pulp: AQ content, 0.005 mmol/g, as made in Example 2.
[c]Aminopropyl silica (Aldrich) AQ (as AQSO₂NH—) content 0.25 mmol/g as made in Example 9.
[d]Aminopropyl silica (Aldrich) AQ content 0.94 mmol/g as made in Example 8.

EXAMPLE 12

Alternating Cycles of Photoreduction and Oxygenation

The reaction vessel was charged with 200 mg of silica AQ (0.02 mmol/g), 10 mL of iPrOH, and a constant stream of nitrogen was passed through the fritt. The reactor was irradiated for 5 min. Alcohol was forced out from the reactor with the aid of nitrogen. Water (5 mL) was introduced and air was bubbled for 3 min. The aqueous solution was filtered and kept. The reaction vessel was flushed with nitrogen and the iPrOH solution was re-introduced and irradiated. After five alternating cycles the aqueous solution contained 0.014 mmol of hydrogen peroxide, i.e. production of 3.5 mol $H_2O_2$/mol AQ.

EXAMPLE 13

Photooxidation of Glycerine

Aqueous glycerine (10 mL, 20% glycerine) was irradiated with 120 mg silica AQ (0.08 mmll/g) for 5 h with air blowing through the mixture. GC analysis determined formation of dihydroxy acetone (0.85 mmol, 17 mol/mol AQ/h).

EXAMPLE 14

Irradiation of Toluene

Toluene (10 mL) and silica AQ (120 mg, 0.08 mmol AQ/g) were irradiated as above (5 h). GC analysis demonstrated the formation of benzaldehyde (44 mg, 0.36 mmol, 4.5 mol/mol AQ) as well as benzoic acid. Analysis of the toluene by the iodometric method showed that 0.4 mmol (5 mol/mol AQ) of peroxide was formed.

EXAMPLE 15

Preparation of Acrylic Acid 2-Isopropenyl Anthraquinone Copolymer 2-isopropenyl AQ (0.3 g), 1.2 g acrylic acid (Aldrich, containing inhibitors (200 ppm MEHQ) and 40 mg AIBN were placed in a heavy-walled glass tube. Oxygen was removed by three freeze/thaw cycles. The tube was sealed and heated to 80° C. for 1 h. The polymer thus obtained was dissolved in dioxane. TLC (20% AcOEt in hexane) shows disappearance of free isopropenyl AQ.

EXAMPLE 16

Binding of Poly(Acrylic) 2-Isopropenyl AQ to Silica APTS

Silica 60 APTS (2 g) was added to 20 mL dry dioxane solution containing 0.5 g of polymer. Dicyclohexyl carbodiimide (DCC) 85 mg was added and the mixture was stirred overnight, then filtered and washed with dioxane ethanol, acetone and dried. Irradiation of 20% aqueous isopropanol for 1 h as in Example 9 yielded 0.08 mmol $H_2O_2$ in the effluent from the catalyst.

EXAMPLE 17

Solar Irradiation

The procedure of Example 11a was repeated except that the reactor was placed in bright summer sunlight for 5 h. The yield of hydrogen peroxide was 0.28 mmol.

EXAMPLE 18

Preparation of Methyl Methacrylate-Acrylic Acid 2-Isopropenyl Anthraquinone Terpolymer 2-isopropenyl AQ (0.3 g), 0.5 g acrylic acid and 0.7 g methyl acrylate (Aldrich) containing inhibitor (200 ppm methyl hydroquinone, MeHQ) and 40 mg 2,2'-azobis-isobutyronitrile (AIBN) were placed in a heavy-walled glass tube. Oxygen was removed by three freeze/thaw cycles. The tube was sealed and heated to 80° C. for 1 h. The polymer thus obtained was dissolved in dioxane. TLC (20% AcOEt in hexane) shows disappearance of free isopropenyl AQ.

A 1% solution of the polymer in dioxane was sprayed on filter paper (Whatman #1) and dried. The filter paper was cut into small square pieces (ca. 5×5 mm). The impregnated paper pieces were suspended in the 20%, iPrOH water mixture and irradiated as in Example 11 for 1 h. Hydrogen peroxide (0.07 mmol) was produced.

EXAMPLE 19

Preparation of Hydrogen Peroxide via Reduction with Soluble Agents

Experiments were performed in a small glass reactor equipped with a fritted glass at the bottom, an inlet side arm and tap, and capped with a septum. Nitrogen or air was supplied through the side arm and the fritt, stirring the reaction mixture and forming either an inert or oxidative atmosphere. The reactor was vented through the septum by a hypodermic needle. Washing was performed by injecting degassed solvent through the septum with a syringe. The solvents were forced out through fritt and tap by applying nitrogen through the septum. All reactions were carried out at room temperature.

The reactor was charged with functionalized silica and solvent under a nitrogen atmosphere. A solution of the reducing agent was injected onto the suspended silica. Immediate reaction took place, as evidenced by rapid color change from yellow to dark or deep red. Solvent was filtered after 5 min. and the silica washed 3 times with (degassed) water. A new portion of water was added and air applied through the side arm and fritt. When the color reverted to yellow the liquid was forced out, collected and hydrogen peroxide determined. This procedure was repeated several times with the same sample of modified silica. Results of are given in the Table 2 below.

TABLE 2

Hydrogen Peroxide Formation by Chemical Reduction and Air Oxidation of Immobilized AQ Function

| Reducing agent $H_2O_2$— | Aminopropyl silica modified with | | | | | |
|---|---|---|---|---|---|---|
| | I | | II | | III | |
| | mmol/g | % | mmol/g | % | mmol/g | % |
| $NaBH_4$ | 0.7[a] | 14 | 0.16[a] | 32 | 0.105[a] | 16 |
| | | | | | 0.085[a] | 17 |
| $Na_2S_2O_4$ | 0.0215[a] | 4.3 | 0.039[a] | 8 | 0.190[a] | 38 |
| | | | 0.036[b] | 7 | 0.02[c] | 4 |
| $NaCNBH_3$ | 0.014[a] | 2.8 | 0.002[f,d] | 0.05 | 0.021[a] | 4.3 |
| $Na_2SO_3$ | | | | | 0.0016[a] | 0.5 |

[a]In water.
[b]In dimethyl formamide.
[c]In ethanol.
[d]Water + $NaCO_3$.
[e]In tetrahydrofuran.
[f]Pyridine added.

EXAMPLE 20

Hydrogenation of Immobilized Anthraquinones Catalyzed by Pentacyanocobaltate

The experiments were performed in an atmospheric pressure hydrogenation line. Provisions were made to store all reagents in the system and transferring them to the reaction site under hydrogen atmosphere.

Cobalt chloride hexahydrate (70 mg, 0.29 mmol) in 2 mL of water were placed in a reaction vessel. Air was removed and the system charged with hydrogen and stirred. Sodium hydroxide (2 mL, 0.1N) was added, and after several minutes a solution of potassium cyanide (100 mg, 1.53 mmol) was added. The mixture was stirred for 1 h. Aminopropyl silica modified with III (0.5 g) was suspended in 5 ml of water. One-ml portions of this suspension were transferred to the reaction vessel at 15-min intervals. A sharp color change from yellow to dark red occurred upon the addition of the first portion. Thirty minutes after the addition of the last portion, the reaction was terminated. Hydrogen was pumped off and the system was maintained under argon. Solvents were removed and the silica was washed five times with degassed water. A fresh portion of water was added and air was blown through the mixture until the silica regained a yellow color. The water was collected and hydrogen peroxide determined. The amount measured was 0.35 mmol (14%).

Similar experiments with silica modified by II yielded 0.4 mmol (16%) and with I yielded 0.045 mmol (18%).

EXAMPLE 21

Hydrogenation of Immobilized Anthraquinones Catalyzed by Palladium Chloride

Experiments were carried out in an atmospheric pressure hydrogenation system, as described above. Palladium chloride (24 mg, 0.13 mmol) in DMF (5 mL) were stirred in the reaction vessel. Air was removed, and hydrogen charged. After 0.5 h, hydrogen consumption ceased.

Aminopropyl silica (0.5 g) modified with I was suspended in DMF. This was added under a hydrogen atmosphere and stirred for an additional 1.5 h. Reaction was terminated by removal of hydrogen and application of argon.

The solvent was removed and the remaining silica was washed three times with degassed water. A fresh portion of water was added and air blown. The aqueous solution was collected and hydrogen peroxide determined. 0.01 mmol (4%) hydrogen peroxide was formed.

A similar reaction, with silica modified by II produced 0.017 (7%) mmol of hydrogen peroxide.

REFERENCES

1. Tickle and F. Wilkinson, Trans. Farad. Soc., 61, 1981 (1965).
2. V. P. Foyle, Y. Takahashi and J. E. Guillet, J. Polym. Sci., Polym. Chem. Ed., 30, 257 (1992).
3. E. G. R. L. Chowdhury and E. Backvoll, J. Chem. Soc., Chem. Commun. 1063 (1991).
4. G. W. Parshall, "Homogeneous Catalysis", Wiley-Interscience, New York; B. R. James, "Homogeneous Hydrogenation", Wiley-Interscience, New York; F. J. McQuillin, "Homogeneous Hydrogenation in Organic Chemistry", D. Riedel, Dordrecht.
5. A. M. Aquino, C. J. Abelt, K. L. Berger, C. M. Darraguh, S. E. Kelly and M. V. Cossette, J. Amer. Chem. Soc., 112, 5819 (1990).
6. Colorimetric Determination of Non-metals, D. F. Boltz and J. Howell, eds., Wiley, 19, p. 301.

What is claimed is:

1. A process for producing hydrogen peroxide, which comprises reacting oxygen, in the presence of a liquid solvent, with supported anthrahydroquinone moieties bound to a macromolecular inert support, so as to oxidize the supported anthrahydroquinone moieties to supported anthraquinone moieties with formation of hydrogen peroxide, and recovering the hydrogen peroxide so formed as a solution thereof in said liquid solvent, the supported anthraquinone being insoluble in said liquid solvent under conditions of hydrogen peroxide solution recovery.

2. The process of claim 1, wherein the supported anthrahydroquinone moieties are prepared by reduction of supported anthraquinone moieties bound to said support, using a hydrogen-donating organic substrate.

3. The process of claim 2, wherein the support is silica, glass, polyethylene or cellulose.

4. The process of claim 3 wherein the support is silica or glass.

5. The process of claim 1, wherein the supported anthrahydroquinone moieties are prepared by reaction of supported anthraquinone moieties with a soluble reducing agent.

6. The process of claim 5, wherein the soluble reducing agent is sodium borohydride, sodium dithionite, sodium cyanoborohydride or sodium sulphite.

7. The process of claim 1, wherein the supported anthrahydroquinone moieties are prepared by catalytic hydrogenation of supported anthraquinone moieties using a homogeneous catalyst.

8. The process of claim 7, wherein the homogeneous catalyst is ruthenium triphenylphosphine complex, cobalt pentacyanide or palladium chloride.

9. A two-stage process for the production of hydrogen peroxide, which comprises:

in a first stage, reacting a hydrogen-donating organic substrate with supported anthraquinone moieties bound to an inert macromolecular support so as to reduce the supported anthraquinone moieties to supported anthrahydroquinone moieties;

and, in a second stage, reacting the supported anthrahydroquinone moieties with oxygen so as to produce hydrogen peroxide and to re-form supported anthraquinone moieties ready for further reaction in a repeated said first stage.

10. A solid, immobilized anthraquinone derivative comprising:

an inorganic silica or glass supporting material having anthraquinone moieties chemically attached thereto through covalent linkages, the anthraquinone moieties having free, reducible oxo groups;

the immobilized anthraquinone derivative being chemically reducible to its corresponding immobilized anthrahydroquinone derivative which in turn is chemically oxidizable to said anthraquinone derivative to provide a cyclic reduction-oxidation process;

both said derivatives being substantially insoluble in aqueous liquids, polar organic liquids and non-polar organic liquids so as to form a solid phase in reaction mixtures utilizing such liquids as the reaction medium.

11. The derivative of claim 10 wherein the anthraquinone moieties are lower alkyl substituted anthraquinone groups.

12. The derivative of claim 10 wherein the covalent linkages of the anthraquinone groups to the silica support include amide linkages.

13. The derivative of claim 10 wherein the covalent linkages of the anthraquinone groups to the silica support include sulfonamide linkages.

14. A process of preparing immobilized anthraquinone derivatives, which comprises treating solid silica or glass with a silane coupling compound carrying a functional group so as to produce functional group-derivatized silica, and covalently bonding thereto a substituted anthraquinone via the respective functional groups.

15. The process of claim 14 wherein the silane coupling compound carries amino functional groups.

16. The process of claim 15 wherein the substituted anthraquinone is selected from the group consisting of anthraquinone carboxylic acid, anthraquinone carboxylic acid chloride, anthraquinone-sulphonic acid, anthraquinone-disulphonic acid and anthraquinone-acid copolymer.

17. The process of claim 16 wherein the amino-silane coupling compound is amino propyl trimethoxysilane.

* * * * *